(12) United States Patent
Brandes et al.

(10) Patent No.: US 6,365,195 B2
(45) Date of Patent: Apr. 2, 2002

(54) FUNGICIDAL ACTIVE COMPOUND COMBINATIONS

(75) Inventors: Wilhelm Brandes, Leichlingen; Heinz-Wilhelm Dehne, Monheim; Stefan Dutzmann, Hilden; Karl-Heinz Kuck, Langenfeld; Bernd-Wieland Krüger, Bergisch Gladbach, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/736,917

(22) Filed: Dec. 14, 2000

Related U.S. Application Data

(62) Division of application No. 09/541,950, filed on Apr. 3, 2000, now Pat. No. 6,235,744, which is a division of application No. 09/249,690, filed on Feb. 12, 1999, now Pat. No. 6,071,940, which is a division of application No. 08/846,872, filed on May 1, 1997, now Pat. No. 5,922,762, which is a division of application No. 08/629,245, filed on Apr. 8, 1996, now Pat. No. 5,672,619, which is a division of application No. 08/462,408, filed on Jun. 5, 1995, now Pat. No. 5,532,262, which is a continuation of application No. 08/232,923, filed on Apr. 25, 1994, now abandoned.

(30) Foreign Application Priority Data

Apr. 28, 1993 (DE) ........................................ P 43 13 867

(51) Int. Cl.$^7$ .................. A01N 59/02; A01N 37/18; A01N 43/54
(52) U.S. Cl. ................... 424/713; 424/705; 514/275; 514/613
(58) Field of Search ............................... 424/713, 705; 514/275, 613

(56) References Cited

U.S. PATENT DOCUMENTS

| 5,059,623 A | 10/1991 | Kruger et al. | ............... 514/613 |
| 5,166,392 A | 11/1992 | Kruger et al. | ............... 558/271 |

FOREIGN PATENT DOCUMENTS

DE    3 431 856    3/1986

OTHER PUBLICATIONS

Worthing, et al., The Pesticide Manuals, 9$^{th}$ Ed. (1991), pp. 86, 119–120, 123–124, 159–160, 249, 402–403, 431–432, 785, 831–834.
Abstract of DE 3,431,856 Jun. 3, 1986.

*Primary Examiner*—Allen J. Robinson
(74) *Attorney, Agent, or Firm*—Norris McLaughlin & Marcus

(57) ABSTRACT

There are described new active compound combinations of a compound of the formula (I)

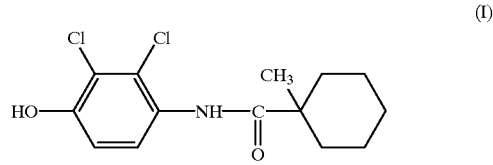

(I)

with known fungicidal active compounds, and their use for the control of phytopathogenic fungi.

5 Claims, No Drawings

FUNGICIDAL ACTIVE COMPOUND COMBINATIONS

This is a divisional application of U.S. Ser. No. 09/541,950, filed Apr. 3, 2000, now U.S. Pat. No. 6,235,744 which is a divisional of U.S. Ser. No. 09/249,690 filed on Feb. 12, 1999, now U.S. Pat. No. 6,071,940, which is a divisional of U.S. Ser. No. 08/846,872, filed on May 1, 1997, now U.S. Pat. No. 5,922,762, which is a divisional of application Ser. No. 08/629,245, filed on Apr. 8, 1996, now U.S. Pat. No. 5,672,619, which is a divisional of application Ser. No. 08/462,408, filed on Jun. 5, 1995, now U.S. Pat. No. 5,532,262, which is a continuation of application Ser. No. 08/232,923, filed on Apr. 25, 1994, now abandoned.

The present application relates to novel active compound combinations which consist of a compound of the formula I (I)

on the one hand and other known fungicidal active compounds on the other hand and are very highly suitable for the control of phytopathogenic fungi.

It is already known that the compounds of the formula (I) has fungicidal properties (cf. EP-A 339,418). The activity of this substance is good; however, in some cases it leaves something to be desired at low application rates.

It is also already known that numerous azole derivatives, aromatic carboxylic acid derivatives, morpholine compounds and other heterocycles can be employed for the control of fungi (cf. K. H. Büchel "Pflanzenschutz und Schädlingsbekämpfung" [Plant protection and pest control] pages 87, 136, 140, 141 and 146 to 153, Georg Thieme Verlag, Stuttgart 1977).

The action of the substances concerned, however, is not always satisfactory at low application rates.

It has now been found that the new active compound combinations of a compound of the formula I (I)

and
(A) dichlofluanid of the formula $(CH_3)_2N-SO_2-N-S-CCl_2F$ (II)

and/or (B) tolylfluanid of the formula $(CH_3)_2N-SO_2-N-S-CCl_2F$ $CH_3$ (III)

and/or (C) tetrachloro-isophthalo-dinitrile of the formula (IV)

(CHLOROTHALONIL)

and/or (D) propineb of the formula $[-Zn-S-CS-NH-CH_2-CH(CH_3)-NH-CS-S-]_n$ (V)

and/or (E) tetramethyl-thiuram disulphide of the formula $(CH_3)_2N-C(=S)-S-S-C(=S)-N(CH_3)_2$ (THIRAM)

(VI)

and/or (F) mancozeb of the formula (VI)

and/or (G) anilazine of the formula

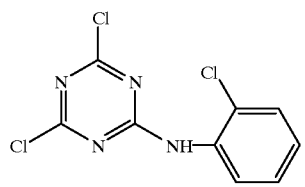
(VII)

and/or (E) copper oxychloride and/or (I) captan of the formula

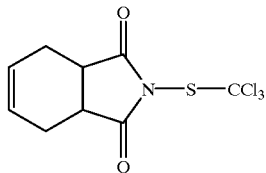
(VIII)

and/or (K) a morpholine derivative of the formula

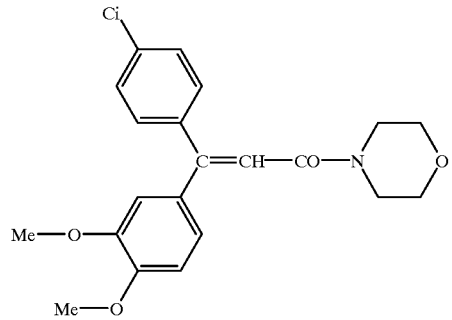
(IX)

(dimetomorph)

and/or (L) dithianone of the formula

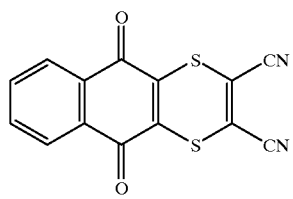
(X)

and/or (M) phaltan of the formula

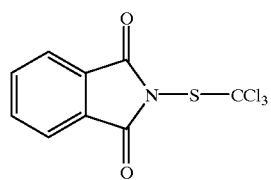
(XI)

and/or (N) cymoxanil of the formula $$CH_3-CH_2-NH-\overset{O}{\underset{}{C}}-NH-\overset{O}{\underset{}{C}}-\overset{CN}{\underset{}{C}}=NOCH_3$$
(XII)

and/or (O) methyl benzimidazole-2-carbamate of the formula

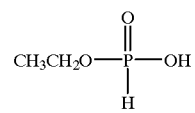
(XIII)

(CARBENDAZIM)

and/or (P) fosetyl of the formula

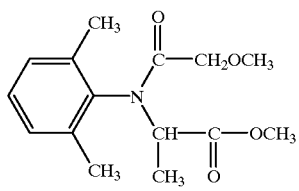
(XIV)

or its aluminium adduct and/or (Q) metalaxyl of the formula (XV)

and/or (R) oxadixyl of the formula

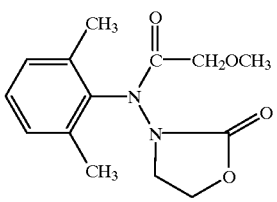
(XVI)

and/or (S) fluazinam of the formula

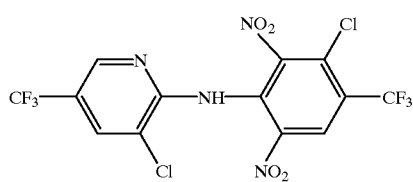
(XVII)

and/or (T) 1-(4-chlorophenyl)-4,4-dimethyl-3-(1,2,4-triazol-1-yl-ethyl)-pentan-3-ol of the formula

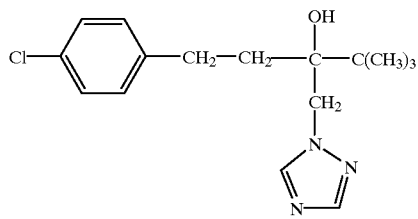
(XVIII)

(TEBUCONAZOLE)

and/or (U) an azole derivative of the formula

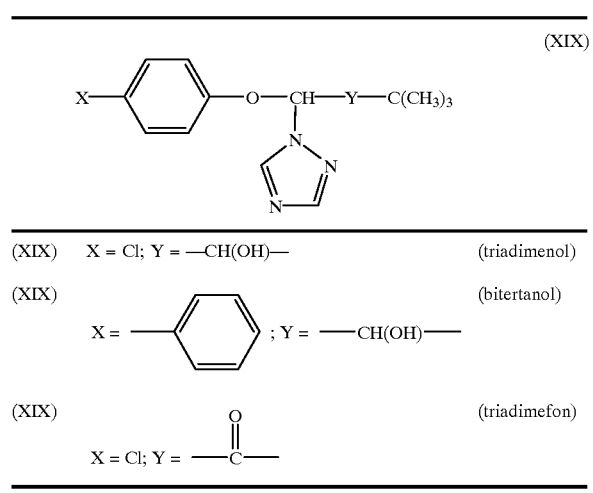
(XIX)

and/or (V) an azole derivative from the group consisting of
  a) difenconazole
  b) penconazole
  c) flusilazole
  d) hexaconazole
  e) myclobutanil
  f) prochloraz
  g) fluquinconazole
  h) epoxiconazole
  i) fenpropidin
  j) perifenox
  k) 8-t-butyl-2-(N-ethyl-N-n-propylamino)-methyl-1,4-dioxaspiro[4,5]decane and/or
(W) metiram and/or
(X) pyrimethanil and/or
(Y) diethofencarb and/or
(Z) mepanipyrim and/or cyprodinyl and/or
(α) phenylpyrrole and/or
(β) iprodione and/or
(Γ) vinclozolin and/or
(δ) procymidone and/or
(ε) benomyl and/or
(θ) thiphanate and/or thiophanate-methyl and/or
(II) sulphur and/or
(n) compounds of the formula a)

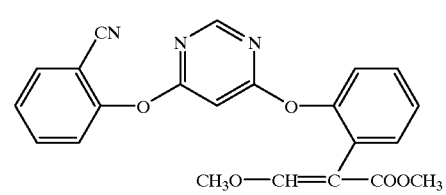

b)

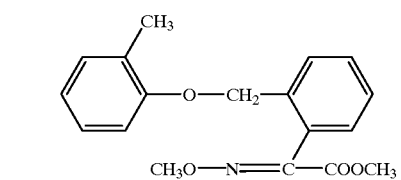

c)

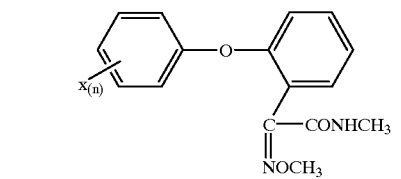

x = F, Cl, Br, CH$_3$; n = 0–3 and/or d)

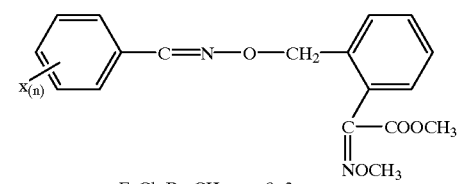

x = F, Cl, Br, CH$_3$; n = 0–3 have very good fungicidal properties.

The active compound of the formula (I) is known (EP-A-339,418). The components additionally present in the combinations according to the invention are also known.

In addition to the active compound of the formula (I), the active compound combinations according to the invention contain at least one active compound from the compounds of the groups (A) to (II). They may also moreover contain further fungicidally active admixed components.

If the active compounds are present in the active compound combinations according to the invention in certain weight ratios, the synergistic effect is seen particularly distinct. However, the weight ratios of the active compounds in the active compound combinations can be varied with a relatively wide range. In general, the following are proportioned to 1 part by weight of active compound of the formula (I)

0.5 to 50 parts by weight, preferably
0.5 to 10 parts by weight of active compound propineb (D)
0.5 to 50 parts by weight, preferably
0.5 to 10 parts by weight of active compound mancozeb (F)
0.5 to 50 parts by weight, preferably
0.5 to 10 parts by weight of active compound TMTD (E)
0.5 to 50 parts by weight, preferably
0.5 to 10 parts by weight of active compound metiram (W)
0.5 to 50 parts by weight, preferably
0.5 to 20 parts by weight of active compound dichlofluanid (A)
0.5 to 50 parts by weight, preferably
0.5 to 20 parts by weight of active compound tolylfluanid (B)
0.5 to 50 parts by weight, preferably
0.5 to 20 parts by weight of active compound phaltan (M)
0.5 to 50 parts by weight, preferably
0.5 to 20 parts by weight of active compound captan (I)
1 to 50 parts by weight, preferably
1 to 20 parts by weight of active compound Cu oxychloride (H)
1 to 50 parts by weight, preferably
1 to 20 parts by weight of active compound sulphur (II)
0.5 to 50 parts by weight, preferably
0.5 to 10 parts by weight of active compound anailazine (G)
0.5 to 50 parts by weight, preferably
0.5 to 10 parts by weight of active compound chlorothalonil (C)
0.5 to 50 parts by weight, preferably
0.5 to 10 parts by weight of active compound dithianon (L)
0.1 to 10 parts by weight, preferably
0.5 to 5 parts by weight of active compound fluazinam (S)
0.1 to 10 parts by weight, preferably
0.5 to 5 parts by weight of active compound pyrimetanil (X)
0.1 to 10 parts by weight, preferably
0.5 to 5 parts by weight of active compound diethofencarb (Y)
0.1 to 10 parts by weight, preferably
0.5 to 5 parts by weight of active compound mepanipyrin (Z)
0.1 to 10 parts by weight, preferably
0.5 to 5 parts by weight of active compound phenylpyrrole (Saphire) (α)
0.1 to 20 parts by weight, preferably
0.5 to 10 parts by weight of active compound iprodione (β)
0.1 to 20 parts by weight, preferably
0.5 to 10 parts by weight of active compound vinclozolin (γ)
0.1 to 20 parts by weight, preferably
0.5 to 10 parts by weight of active compound procymidone (δ)
0.1 to 10 parts by weight, preferably
0.25 to 5 parts by weight of active compound benomyl (ε)
0.1 to 10 parts by weight, preferably
0.25 to 5 parts by weight of active compound carbendazim (O)
0.1. to 10 parts by weight, preferably
0.25 to 5 parts by weight of active compound thiopanate-methyl (ω)
0.1 to 10 parts by weight, preferably
0.25 to 5 parts by weight of active compound cymoxanil (N)
0.1 to 10 parts by weight, preferably
0.25 to 5 parts by weight of active compound metalaxyl (Ω)
0.1 to 10 parts by weight, preferably
0.25 to 5 parts by weight of active compound oxadixyl (R)
0.1 to 10 parts by weight, preferably
0.2 to 5 parts by weight of active compound dimethomorph (K)
0.1 to 20 parts by weight, preferably
0.2 to 10 parts by weight of active compound A1 fosethyl (P)
0.01 to 10 parts by weight, preferably
0.025 to 5 parts by weight of active compound tebuconazole (T)

-continued 0.01 to 10 parts by weight, preferably
0.025 to 5 parts by weight of active compound triadimefon (U XIXc)
0.01 to 10 parts by weight, preferably
0.025 to 5 parts by weight of active compound triadimenol (U XIXa)
0.01 to 10 parts by weight, preferably
0.025 to 5 parts by weight of active compound bitertanol (U XIXb)
0.01 to 10 parts by weight, preferably
0.025 to 5 parts by weight of active compound difenconazole (Va)
0.01 to 10 parts by weight, preferably
0.025 to 5 parts by weight of active compound penconazole (Vb)
0.01 to 10 parts by weight, preferably
0.025 to 5 parts by weight of active compound flusilazole (Vc)
0.02 to 10 parts by weight, preferably
0.025 to 5 parts by weight of active compound hexaconazole (Vd)
0.01 to 10 parts by weight, preferably
0.025 to 5 parts by weight of active compound myclobutanil (Ve)
0.01 to 10 parts by weight, preferably
0.025 to 5 parts by weight of active compound prochloraz (Vf)
0.01 to 10 parts by weight, preferably
0.025 to 5 parts by weight of active compound of formula (ηa)
0.01 to 10 parts by weight, preferably
0.025 to 5 parts by weight of active compound of formula (ηb)

The active compound combinations according to the invention have very good fungicidal properties and can be employed in particular for the control of phytopathogenic fungi, such as Plasmodiophoromycetes, Oomycetes, Chytridiomycetes, Zygomycetes, Ascomycetes, Basidiomycetes, Deuteromycetes etc.

The active compound combinations according to the invention are very particularly suitable for the control of cereal diseases, such as Erysiphe, Cochliobolus, Pyrenophora and Leptosphaeria, and against fungal attack on vegetables, grapes and fruit, for example against Venturia on apples, Botrytis on beans and Phytophthora on tomatoes.

The good plant tolerability of the active compound combinations in the concentrations necessary for the control of plant diseases enables a treatment of above-ground parts of plants, of plants and seeds, and of the soil.

The active compound combinations according to the invention can be converted into the customary formulations, such as solutions, emulsions, suspensions, powders, foams, pastes, granules, aerosols, very fine capsules in polymeric substances and in coating compositions for seeds, as well as ULV formulations.

These formulations are produced in a known manner, for example by mixing the active compounds or the active compound combinations with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks. As emulsifying, and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound combinations according to the invention can be present in the formulations as a mixture with other known active compounds, such as fungicides, insecticides, acaricides and herbicides, as well as in mixtures with fertilizers or plant growth regulators.

The active compound combinations can be used as such or in the form of their formulations or the use forms prepared therefrom, such as ready-to-use solutions, emulsifiable. concentrates, emulsions, suspensions, wettable powders, soluble powders and granules.

They are used in the customary manner, for example by watering, spraying, atomizing, scattering, dusting, brushing on, as a powder for dry seed treatment, as a solution for seed treatment, as a water-soluble powder for seed treatment, as a water-dispersible powder for slurry treatment, or seed-coating.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the site of action.

The good fungicidal action of the active compound combinations according to the invention can be seen from the following Examples. While the individual active compounds have weaknesses in their fungicidal action, the combinations exhibit an action which extends beyond a simple additive action.

A synergistic effect is always present with fungicides if the fungicidal action of the active compound combinations is greater than the sum of the actions of the individually applied active compounds.

The action to be expected for a given combination of two active compounds can be calculated (cf. Colby, S. R., "Calculating Synergistic and Antagonistic Responses of Herbicide Combinations", Weeds 15, pages 20–22, 1967) as follows:

X denotes the degree of efficacy, expressed in % of the untreated control, on use of the active compound A at a concentration of m ppm, Y denotes the degree of efficacy, expressed in % of the untreated control, on use of the active compound B at a concentration of m ppm, E denotes the expected degree of efficacy, expressed in % of the untreated control, on use of the active compound A and B at a concentrations of m and n ppm, $$\text{then} \quad E = X + Y - \frac{X \cdot Y}{100}.$$

If the actual fungicidal action is larger than calculated, the combination is superadditive in its action, i.e. a synergistic effect is present. In this case, the actually observed degree of efficacy must be greater than the value for the expected degree of efficacy (E) calculated from the abovementioned formula.

EXAMPLE 1

Botrytis Test (Bean)/Protective

To produce a suitable preparation of active compound, commercially available active compound formulations (individual active compounds or active compound combinations) are diluted with water to the desired concentration in each case.

To test for protective activity, young plants are sprayed with the preparation of active compound until dripping wet. After the spray coating has dried on, 2 small pieces-of agar covered with *Botrytis cinerea* are placed on each leaf. The inoculated plants are placed in a darkened humid chamber at 20° C.

3 days after the inoculation, the size of the infected spots on the leaves is evaluated.

In order to demonstrate synergism between the active compounds used in this test, the results were assessed by the method described by Colby (see above).

Active compounds, active compound concentrations and test results can be seen from the following tables.

TABLE 1

Botrytis test (bean)/protective

| Active compound | Active compound concentration in ppm | Degree of effectiveness in % of the untreated control |
| --- | --- | --- |
| (I) *[2,3-dichloro-4-hydroxyphenyl-NH-CO-1-methylcyclohexyl]* | 5 | 51 |
| Dichlofluanid $(CH_3)_2$—N—$SO_2$—N(Ph)—S—$CCl_2F$ | 100 | 32 |

Mixture according to the invention

| | | |
| --- | --- | --- |
| (I) + Dichlofluanid | 5 + 100 | 89 |
| Expected value, calculated by the Colby formula (see above) | | 67 |

Botrytis test (bean)/protective

| Active compound | Active compound concentration in ppm | Degree of effectiveness in % of the untreated control |
| --- | --- | --- |
| (I) *[2,3-dichloro-4-hydroxyphenyl-NH-CO-1-methylcyclohexyl]* | 5 | 51 |
| Procymidone *[3,5-dichlorophenyl-N-(1,2-dimethylcyclopropane-1,2-dicarboximide)]* | 50 | 44 |

Mixture according to the invention

| | | |
| --- | --- | --- |
| (I) + Procymidone | 5 + 50 | 91 |
| Expected value, calculated by the Colby formula (see above) | | 73 |

TABLE 1-continued

Botrytis test (bean)/protective

| Active compound | Active compound concentration in ppm | Degree of effectiveness in % of the untreated control |
|---|---|---|
| (I) | 5 | 51 |

[Structure: 2,3-dichloro-4-hydroxyphenyl NH-CO-C(Me)(cyclohexyl)]

| Phaltan | 50 | 0 |

[Structure: phthalimide N-S-CCl₃]

Mixture according to the invention

| (I) + Phaltan | 5 + 50 | 73 |
| Expected value, calculated by the Colby formula (see above) | | 51 |

Botrytis test (bean)/protective

| Active compound | Active compound concentration in ppm | Degree of effectiveness in % of the untreated control |
|---|---|---|
| (I) | 5 | 51 |

[Structure: 2,3-dichloro-4-hydroxyphenyl NH-CO-C(Me)(cyclohexyl)]

| Fluazinam | 5 | 20 |

[Structure: 3-chloro-5-trifluoromethylpyridin-2-yl-NH-(2,6-dinitro-3-chloro-4-trifluoromethylphenyl)]

Mixture according to the invention

| (I) + | 5 + | 99 |

TABLE 1-continued

| | | |
|---|---|---|
| Fluazinam | 5 | |
| Expected value, calculated by the Colby formula (see above) | | 61 |

Botrytis test (bean)/protective

| Active compound | Active compound concentration in ppm | Degree of effectiveness in % of the untreated control |
|---|---|---|
| (I) | 5 | 51 |

[Structure: 2,3-dichloro-4-hydroxyphenyl with NH—CO—C(Me)(cyclohexyl) group]

| | | |
|---|---|---|
| Pyrimethanil | 10 | 0 |

[Structure: 4,6-dimethyl-2-(phenylamino)pyrimidine]

Mixture according to the invention

| | | |
|---|---|---|
| (I) + Pyrimethanil | 5 + 10 | 93 |
| Expected value, calculated by the Colby formula (see above) | | 51 |

Botrytis test (bean)/protective

| Active compound | Active compound concentration in ppm | Degree of effectiveness in % of the untreated control |
|---|---|---|
| (I) | 5 | 51 |

[Structure: 2,3-dichloro-4-hydroxyphenyl with NH—CO—C(Me)(cyclohexyl) group]

| | | |
|---|---|---|
| Carbendazim | 5 | 52 |

[Structure: benzimidazol-2-yl—NH—CO—O—CH$_3$]

Mixture according to the invention

| | | |
|---|---|---|
| (I) + Carbendazim | 5 + 5 | 87 |

TABLE 1-continued

| | |
|---|---|
| Expected value, calculated by the Colby formula (see above) | 76 |

| Botrytis test (bean)/protective | | |
|---|---|---|
| Active compound | Active compound concentration in ppm | Degree of effectiveness in % of the untreated control |
| (I) 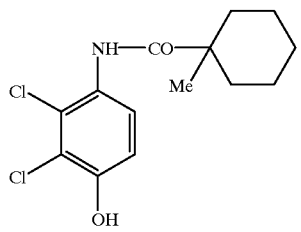 | 5 | 51 |
| Tolylfluanid 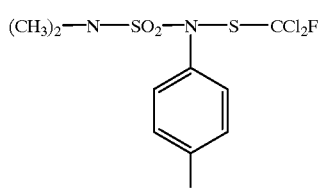 | 50 | 32 |

Mixture according to the invention

| | | |
|---|---|---|
| (I) + Tolylfluanid | 5 + 50 | 84 |
| Expected value, calculated by the Colby formula (see above) | | 67 |

| Botrytis test (bean)/protective | | |
|---|---|---|
| Active compound | Active compound concentration in ppm | Degree of effectiveness in % of the untreated control |
| (I) 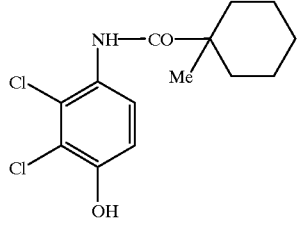 | 5 | 51 |

TABLE 1-continued

| Chlorothalonil | 200 | 37 |
|---|---|---|

Chlorothalonil structure: hexachlorobenzene-derivative with CN groups (2,4,5,6-tetrachloroisophthalonitrile)

Mixture according to the invention

| (I) + Chlorothalonil | 5 + 200 | 73 |
|---|---|---|
| Expected value, calculated by the Colby formula (see above) | | 69 |

EXAMPLE 2

*Leptosphaeria nodorum* Test (Wheat/Protective
Solvent: 100 parts by weight of dimethylformamide
Emulsifier: 0.25 parts by weight of alkylaryl polyglycol ether To produce a suitable preparation of active compound, 1-part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptosphaeria nodorum*. The plants remain for 48 hours in an incubation cabin at 20° C. and 100% relative atmospheric humidity.

The plants are placed in a greenhouse at a temperature of 15° C. and a relative atmospheric humidity of about 80%.

Evaluation is effected 10 days after the inoculation.

In this test, a clearly superior activity compared with the prior art is shown, for example, by the compounds according to the following Preparation Examples:

TABLE 2

Leptosphaeria nodorum test (wheat)/protective

| Active compound | Active compound concentration of the spray liquor in ppm | Degree of effectiveness in % of the untreated control |
|---|---|---|
| Tebuconazole | 25 | 75 |
| (I) | | 0 |
| Tebuconazole + (I) (1:1) | 12,5 + 12,5 | 100 |

EXAMPLE 3

Erysiphe Test (Barley)/Protective
Solvent: 10 parts by weight N-methyl-pyrrolidon
Emulsifier: 0.6 parts by weight alkylarylpoly-glycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *hordei.*

The plants are placed in a greenhouse at a temperature of about 20° C. and a relative atmospheric humidty of about 80%, in order to promote the development of powdery mildew pustules.

Evaluation is carried out 7 days after the inoculation.

In this test, a clearly superior activity compared with the prior art is shown, for example, by the compounds according to the following preparation examples:

EXAMPLE 4

Erysiphe Test (Wheat) Protective

Solvent: 10 parts by weight N-methyl-pyrrolidone

Emulsifier: 0.6 parts by weight alkylarylpoly-glycolether

To produce a suitable preparation of active compound, 1-part by weight of active compound is mixed with the stated amounts of solvent and emulsifier, and the concentrate is diluted with water to the desired concentration.

To test for protective activity, young plants are dusted with spores of *Erysiphe graminis* f. sp. *hordei.* 48 hours after the inoculation, the plants are sprayed with the preparation of active compound until dew-moist.

TABLE 3

Erysiphe-Test (barley)/protective

| Active compound | Active compound concentration in g/ha | Degree of effectiveness in % of the untreated control |
|---|---|---|
| 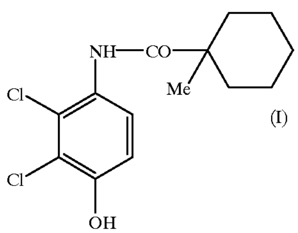  (I) | 50 | 0 |
| 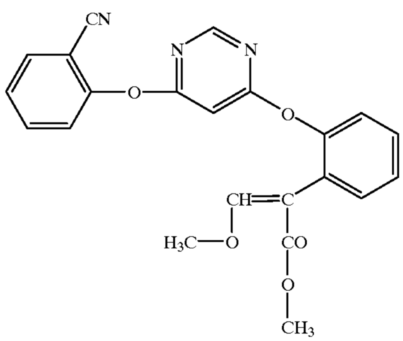  (ηa) | 50 | 15 |
| 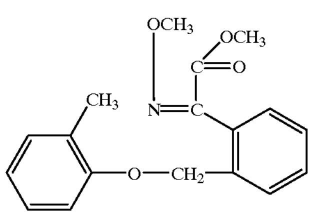  (ηb) | 50 | 85 | mixtures according to the invention:

| | | | |
|---|---|---|---|
| (I) + (ηb) | | 25 | 100 |
| (1,0:1) | + | 25 | |
| (I) + (ηa) | | 25 | 58 |
| (1,0:1) | + | 25 | |

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples:

stated amounts of solvent and emulsifier, and the concentrate is diluted with water to the desired concentration.

To test for curative activity, young plants are dusted with spores of *Erysiphe graminis* f.sp.*hordei*. 48 hours after the inoculation, the plants are sprayed with the preparation of active compound until dew-moist.

The plants are placed in a greenhouse at a temperature of about 20° C. and a relative atmospheric humidity of about

TABLE 4

Erysiphe Test (wheat) protective

| Active compound | Active compound concentration in g/ha | Degree of effectiveness in % of the untreated control |
|---|---|---|
| known: | | |
| 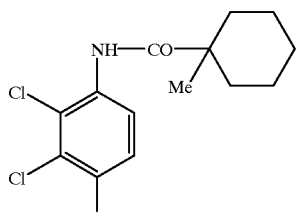 (I) | 200<br>25 | 85<br>30 |
| 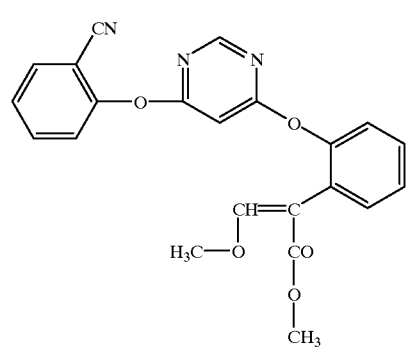 (ηa) | 200 | 79 |
| 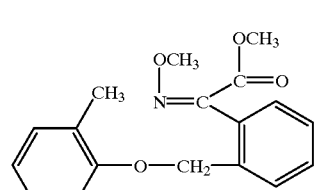 (ηb) | 25 | 85 |
| mixtures according to the invention: | | |
| (I) + (ηb)<br>(1,0:1) | 12,5<br>+ 12,5 | 100 |
| (I) + (ηa)<br>(1,0:1) | 100<br>+ 100 | 94 |

EXAMPLE 5

Erysiphe-Test (Wheat)/Curative
Solvent: 10 parts by weight of N-methyl-pyrrolidone
Emulsifier: 0.6 parts by weight of alkylaryl-polglycolether
To produce a suitable preparation of active compound, 1-part by weight of active compound is mixed with the 80%, in order to promote the development of powdery mildew pustules.

Evaluation is carried out 7 days after the inoculation.

In this test, a clearly superior activity compared with the prior art is shown, for example, by the compounds according to the following preparation examples:

TABLE 5

Erysiphe-test (wheat)/curative

| Active compound | Active compound concentration in g/ha | Degree of effectiveness in % of the untreated control |
|---|---|---|
| (I) 2,3-dichloro-4-hydroxy-phenyl cyclohexyl methyl carboxamide | 200 | 30 |
| (ηa) methoxyacrylate pyrimidine compound | 200 | 75 |

| mixtures according to the invention: | | | |
|---|---|---|---|
| (I) + (ηb) | | 100 | 96 |
| (1,0:1) | + | 100 | |

EXAMPLE 6

*Leptosphaeria nodorum* Test (Wheat)/Curative

Solvent: 10 parts by weight of dimethyl-formamide

Emulsifier: 0.6 parts by weight of alkylaryl polyglycol ether

To produce a suitable preparation of active compound, 1-parts by weight of active compound is mixed with the stated amounts of solvent and emulsifier, and the concentrate is diluted with water to the desired concentration.

To test for curative activity, young plants are sprayed with the preparation of active compound until dew-moist. After the spray coating has dried on, the plants are sprayed with a spore suspension of *Leptosphaeria nodorum*. The plants remain for 48 hours in an incubation cabin at 20° C. and 100% relative atmospheric humidity.

The plants are placed in a greenhouse at a temperature of 15° C. and a relative atmospheric humidity of about 80%.

Evaluation is effected 10 days after the inoculation. In this test, a clearly superior activity compared with the prior art is shown, for example, by the compounds according to the following Preparation Examples:

TABLE 6

Leptosphaeria nodorum-Test (Wheat)/curative

| Active compound | Active compound concentration in g/ha | Degree of activity in % of the untreated control |
|---|---|---|
| (I) — 2,3-dichloro-4-hydroxyphenyl compound with NH—CO—cyclohexyl(Me) group | 400 | 25 |
| (ηb) — compound with OCH₃, OCH₃, C=O, CH₃, N=C, O—CH₂ groups | 400 | 49 | mixtures according to the invention:

| | | | |
|---|---|---|---|
| (I) + (ηb) (1,0:1) | + | 200 200 | 81 |

EXAMPLE 7

*Pyrenophora teres* Test (Barley)/Protective

Solvent: 10 parts by weight N-methyl-pyrrolidon

Emulsifier: 0.6 parts by weight alkylarylpoly-glycolether

To produce a suitable preparation of active compound, 1-part by weight of active compound is mixed with the stated amounts of solvent and emulsifier, and the concentrate is diluted with water to the desired concentration.

To test for protective activity, young plants are sprayed with the preparation of active compound until dew moist. After the spray coating has dried off, the plants are sprayed with a conidia suspension of *Pyrenophora teres*. The plants then remain in an incubation cabin at 20° C. and 100% relative atmospheric humidity for 48 hours.

The plants are placed in a greenhouse at a temperature of about 20° C. and a relative atmospheric humidity of about 80°.

Evaluation is carried out 7 days after inoculation.

In this test, a clearly superior activity compared with the prior art is shown, for example, by the compounds according to the following preparation examples:

TABLE 7

Pyrenophora teres-test (barley)/protective

| Active compound | Active compound concentration in g/ha | Degree of effectiveness in % of the untreated control |
|---|---|---|
| 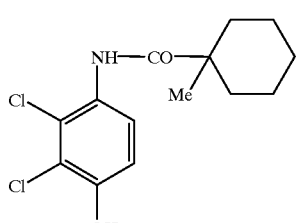 (I) | 25 | 33 |
| 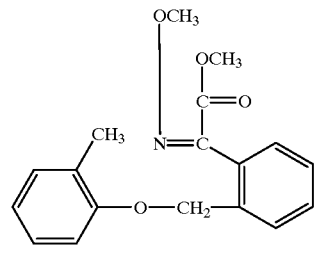 (ηb) | 25 | 33 |
| mixtures according to the invention: | | |
| (I) + (ηb) (1,0:1) | 12,5 + 12,5 | 75 |

What is claimed is:

1. A synergistic fungicidal composition comprising synergistic fungicidally effective amounts of the combination of a compound of the formula:

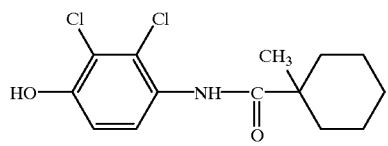 (I)

and a second compound selected from the group consisting of (B) pyrimethanil and sulphur.

2. A composition according to claim 1, wherein the weight ratio of the compound of the formula (I):
   to pyrimethanil is between 1:0.1 and 1:10; or to sulphur is between 1:1 and 1:50.

3. A method of combating fungi which comprises administering to such fungi or to a fungus habitat a synergistic fungicidally effective amount of a composition according to claim 1.

4. The synergistic fungicidal composition according to claim 1, wherein the second compound is (II) sulphur.

5. A method of combating fungi which comprises administering to such fungi or to a fungus habitat a synergistic fungicidally effective amount of a composition according to claim 4.

* * * * *